United States Patent [19]

Hernandez et al.

[11] Patent Number: 4,912,257

[45] Date of Patent: Mar. 27, 1990

[54] PROCESS FOR PREPARATION OF AQUEOUS SOLUTIONS OF 2-HYDROXY-4-METHYLTHIO BUTYRIC ACID

[75] Inventors: Javier A. Hernandez; Luis R. Moreno, both of Burgos, Spain

[73] Assignee: Sociedad de Desarrollo Tecnico Industrial, Spain

[21] Appl. No.: 309,241

[22] Filed: Feb. 13, 1989

[30] Foreign Application Priority Data

Feb. 22, 1988 [ES] Spain ................................ 8800496

[51] Int. Cl.$^4$ ........................................... C07C 147/02
[52] U.S. Cl. ..................................................... 562/581
[58] Field of Search .......................................... 562/581

[56] References Cited

U.S. PATENT DOCUMENTS

| | | | |
|---|---|---|---|
| 2,745,745 | 5/1956 | Blake et al. | 562/581 |
| 2,938,053 | 6/1960 | Blake et al. | 562/581 |
| 3,175,000 | 3/1965 | Gielkans | 562/581 |
| 3,773,927 | 11/1973 | Cummins | 562/581 |
| 4,353,924 | 10/1982 | Baker et al. | 562/581 |

FOREIGN PATENT DOCUMENTS

| | | | |
|---|---|---|---|
| 771153 | 8/1971 | Belgium . | |
| 694610 | 10/1959 | Canada | 562/581 |
| 694650 | 9/1964 | Canada | 562/581 |
| 0142488 | 5/1985 | European Pat. Off. . | |
| 0143100 | 5/1985 | European Pat. Off. . | |
| 393824 | 6/1973 | Spain . | |
| 722024 | 1/1955 | United Kingdom . | |
| 915193 | 1/1963 | United Kingdom . | |

*Primary Examiner*—Bruce Gray
*Attorney, Agent, or Firm*—Stevens, Davis, Miller & Mosher

[57] ABSTRACT

A process is described comprising neutralization with ammonium hydroxide of the reaction mixture generated by the hydrolysis of 2-hydroxy-4-methylthio-butyronitrile by sulphuric acid, so as to obtain an aqueous phase and an organic phase which, once separated, are subjected to evaporation to remove the ammonium sulphate formed. For the aqueous phase, this sulphate is removed as a byproduct; and for the organic phase, it is recirculated to the neutralization vessel. The 2-hydroxy-4-methylthio-butyric acid obtained from the organic phase is subsequently diluted with water and possibly stabilized with sulphuric acid. The product obtained is useful as a food supplement in animal diets.

7 Claims, 1 Drawing Sheet

PROCESS FOR PREPARATION OF AQUEOUS SOLUTIONS OF 2-HYDROXY-4-METHYLTHIO BUTYRIC ACID

FIELD OF THE INVENTION

The present invention relates to an improved process for preparing aqueous solutions of DL-2-hydroxy-4-methylthiobutyric acid. These solutions have less color and odor, a lower viscosity and good thermal stability compared to the same product prepared by other known processes.

BACKGROUND OF THE INVENTION

2-Hydroxy-4-methylthio-butyric acid (HMTBA) has the formula:

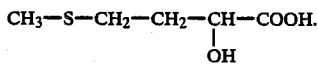

It is a known product similar to the essential amino acid DL-methionine whose principal use is a food supplement for feeding animals. In contrast with the amino acid, it is not used directly by the organism in protein synthesis, because it must be anabolically converted into the amino acid to be used a such. HMTBA is not used in the pure form, but in various forms, namely:

(1) concentrates containing a mixture of calcium and ammonium salts of HMTBA, water and calcium sulphate, as in the U.S. Pat. Nos. 2,745,745 and 2,938,053 and in British Patent Nos. 722,024 and 915,193;

(2) acidic aqueous solutions having a concentration of HMTBA of 85-90% by weight, like that described in the U.S. Pat. Nos. 4,353,924 and 3,773,927; and (3) the calcium salt of HMTBA obtained by the process described in the U.S. Pat. No. 3,175,000.

The general process for obtaining HMTBA from 3-methylthio-propionaldehyde may be summarized by the following scheme:

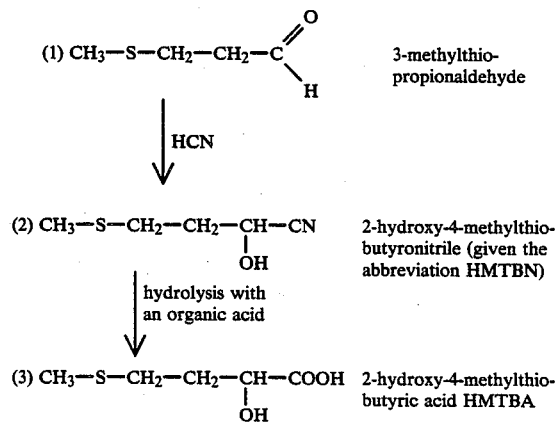

is amply described in the patent bibliography, particularly in the U.S. Pat. Nos. 2,745,745 and 2,938,053 in which step (2)→(3) of the above scheme implies passing through the intermediate amide, which leads to HMTBA by a further hydrolysis. However, depending on the conditions of hydrolysis used, the free acid or the intermediate amide is obtained. This hydolysis reaction of the nitrile is also described in U.S. Pat. Nos. 4,353,924 and 3,175,000 which specifically use sulphuric acid and in U.S. Pat. No. 3,773,927 which uses hydrochloric acid. These patents also describe processing conditions, such as temperature, duration and molar ratios of the inorganic acid to the nitrile. In these patents, once the HMTBA has been obtained by the hydrolysis reaction, it is isolated in the form shown above (salts or aqueous solution) using operations which will be referred to later when comparing the prior art processes with the process of the present invention.

Finally, the European Patent Applications published under Nos. 142,488 and 143,100, both filed on Nov. 13, 1984, particularly relate to obtaining liquid forms of HMTBA by extraction processes with solvents for the HMTBA, from the reaction mixture from hydrolysis of HMTBA carried out in the first case with sulphuric acid and in the second case with an inorganic acid. The two European Patent Applications describe in every detail the conditions which enable solvent extraction to be carried out, as well as the exact nature of the solvents used.

However, these processes of the prior art include various disadvantages derived from the particular manner of carrying out the isolation of the final product HMTBA. These disadvantages can be summarized as follows:

(a) Presence of oligomers of HMTBA with the associated bad odor, color and scarcity of free acid;

(b) Excessive viscosity;

(c) Presence of fine particles of calcium sulphate and/or soluble inorganic salts which render the product impure;

(d) High cost of the final product due to the use of methods such as extraction with solvents; and (e) Low recovery yields of HMTBA.

These disadvantages are overcome by the process according to the invention. It starts from the mixture from the hydrolysis of HMTBA by sulphuric acid in a single step. This enables an aqueous solution of HMTBA to be obtained without the previous disadvantages, due to the use of a novel process for isolating HMTBA in the form of an aqueous solution.

The above references are hereby incorporated by reference.

BRIEF DESCRIPTION OF THE DRAWING

The FIGURE shows a schematic flow diagram for the process of the present invention.

DETAILED DESCRIPTION OF THE INVENTION

Figure 1:
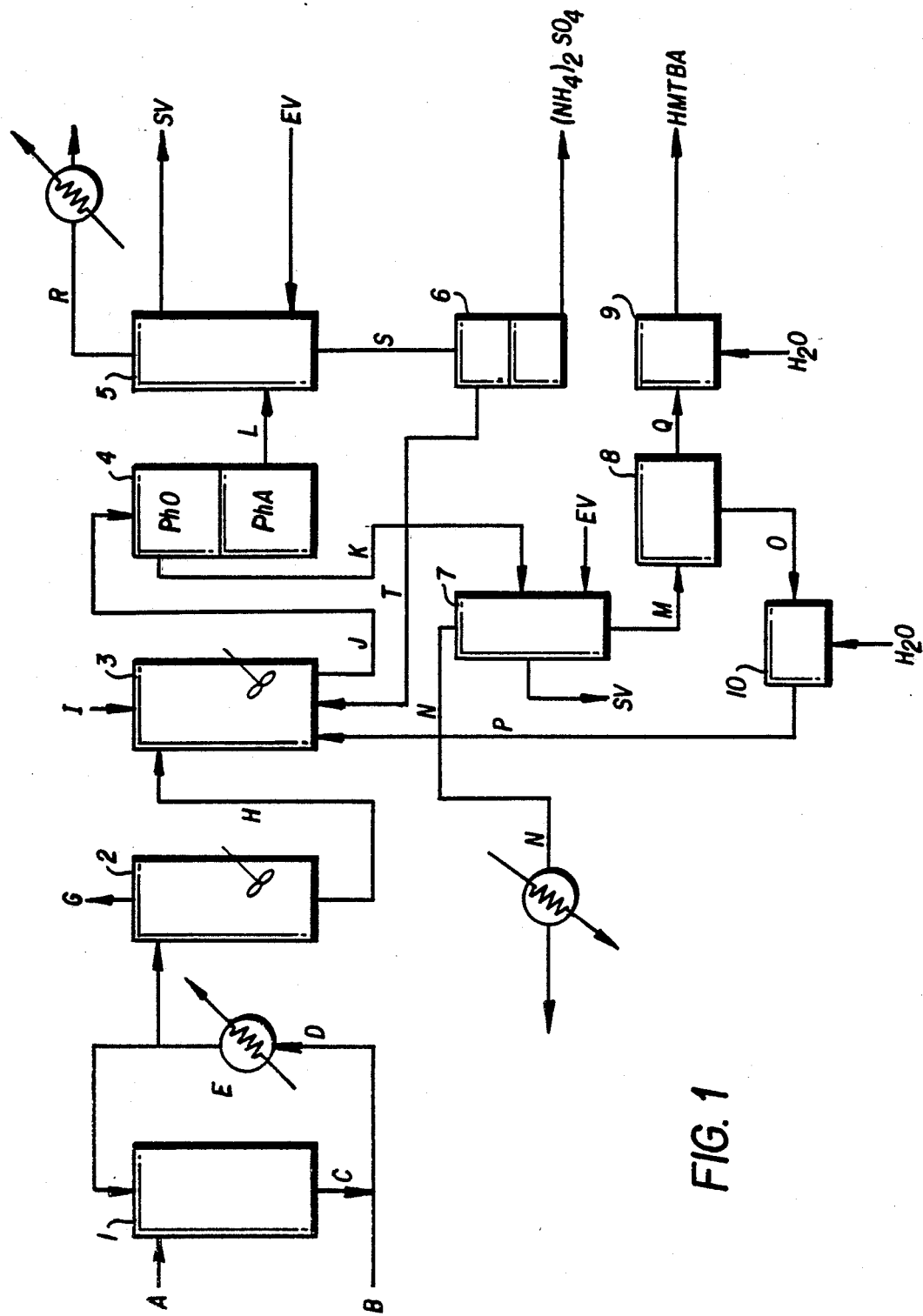

The process for synthesizing 2-hydroxy-4-methylthiobutyronitrile (HMTBA), subsequently described, is a variant of that disclosed in the Spanish Patent No. 393,825 for the synthesis of the amino acid DL-methionine, hereby incorporated by reference. The synthesis of the nitrile is similar in the two processes. The only difference is using an aqueous ammoniacal solution as the reaction medium for obtaining the nitrile corresponding to the amino acid and water not containing ammonia in the case of HMTBN.

The same may be said of the step following the synthesis, namely acidification of HMTBN. In both cases, the product resulting from the synthesis step is placed in contact with concentrated sulphuric acid, preferably a 98% concentration, in an acidification loop in which the two substances are mixed. To avoid local heating leading to the decomposition of the nitrile and the initiation of secondary reactions which produce an increase in coloration, the acidification is carried out continuously with vigorous recirculation, by adding concentrated sulphuric acid to the acidified solution of the nitrile. This solution preferably has a concentration of 20–50% by weight of acid.

As it is necessary to remove heat of dilution of the sulphuric acid, the acidification loop is provided with one or more heat exchangers so that the reaction temperature does not exceed a value of 50° C.

The molar ratio sulphuric acid/HMTBN must be between 0.5 and 2, preferably between 0.8 and 1.5. The proportion of water must be adjusted so that the acidified solution is formed by a single phase and is capable of keeping in solution the ammonium sulphate which will be formed during the subsequent hydrolysis reaction and later neutralization with ammonium hydroxide.

After a contact time of 30–60 minutes, the solution is heated to a temperature of between 60° and 140° C., preferably 90° C. This completes the hydrolysis reaction of the nitrile HMTBN in a single step, without the necessity for using different conditions to obtain the intermediate amide, and of subsequently modifying the conditions to obtain the HMTBA. The duration of the reaction varies between 5 minutes and 6 hours depending on the temperature selected. Thus, for example, using 90° C. and the molar ratio mentioned above, a quantitative conversion of HMTBN to HMTBA is achieved after about 2 hours.

It is extremely important to regulate the temperature and the duration of the reaction within the ranges previously mentioned. This is so because the color and content of oligomers are fundamentally dependent on the values. Temperatures and durations which are greater than those indicated lead to a product with more color and with higher values of viscosity, which is a clear indication of a greater content of oligomers.

During the progress of hydrolysis, it is recommended that a slight vacuum be applied to the reactor (between about 20 and 200 mm). This eliminates the small excess of HCN which is used in the synthesis of HMTBN, as well as volatile impurities which may be formed in the reaction and to which the foul odor of the final product is attributed.

When the hydrolysis reaction is complete, the actual isolation of HMTBA, which forms the essential aspect of the present invention, begins. The reaction mixture from hydrolysis is cooled to 60°–70° C. Its excess acid is neutralized with 20–35% by weight ammonia solution. It is possible to produce the solution in situ if required by bubbling gaseous $NH_3$. The neutralization may require cooling to not exceed the temperature of 60°–70° C.

The neutralized material obtained comprises two phases which may easily be decanted because they have significantly different densities. Thus, the following step of the process is to separate by decantation the organic phase containing 93–95% of the HMTBA produced, from the aqueous phase which holds the remainder. The ammonium sulphate which is formed during the hydrolysis reaction and during neutralization of the aid used in excess, is also partitioned between the two phases. The aqueous phase is the richer with 70–75% by weight.

Separating the two phases by decantation, centrifugation or by another standard process of liquid/liquid separation which does not involve extraction with solvents, is an essential part of the present invention. This extraordinarily simplifies the subsequent purification and total recovery processes for HMTBA, on the one hand, and of ammonium sulphate, on the other hand, with an enhanced yield and an enhanced effectiveness.

Extraction processes using a solvent which is immiscible with water are not necessary. They do not substantially enhance quality or yield, but increase the cost of the process and complicate the equipment.

Starting with the aqueous phase, the ammonium sulphate is precipitated by evaporation of the water at atmospheric pressure or under reduced pressure. The resulting solid is separated by any standard process of solid-liquid separation such as filtration and/or centrifugation. The liquid obtained, containing the part of the ammonium sulphate which was not precipitated and HMTBA, is cycled back to the neutralization vessel. By this process ammonium sulphate is obtained which once dried, has a high purity and is practically devoid of HMTBA. The latter is wholly recovered by recycling prior to the separation process, while remaining part of the organic phase.

The organic phase which is taken from the decanting vessel and contains HMTBA from two streams (neutralization and recycling) is led to a vaporizer, operated under vacuum, where water is evaporated to reduce its content to 1%, preferably to 0.5%, to precipitate the whole of the ammonium sulphate which it contained in solution. The suspension obtained is entirely conveyable, as it contains in suspension only 25–30% of ammonium sulphate produced on the whole in the synthesis and neutralization steps. It can be separate by filtration and/or centrifugation with great ease. The HMTBA obtained by this process has a high purity and its content of ammonium sulphate is less than 1%.

The cake of ammonium sulphate taken from the separating system mentioned above contains quantities of HMTBA varying between 15–30% by weight. The two products are recovered by recycling them to the neutralization vessel by prior dissolution with water. In the same way as for the previous recycling, the ammonium sulphate dissolved is preferentially incorporated in the aqueous phase and the HMTBA in the organic phase, with the result that recovery of the two products is quantitative.

The HMTBA obtained by this process must later be diluted with water an possibly stabilized with a small quantity of sulphuric acid. This gives a solution containing 65–95% of HMTBA and between 0.1 and 0.5% of free sulphuric acid. The solution obtained in this way is in equilibrium with its polymeric or oligomeric esters and is stable over time. In the final product, the ratio of HMTBA monomer to total oligomers is greater than 3. Its coloration is less than 2,000 degrees APHA. Its ammonium sulphate content is less than 1% by weight.

For illustrative purposes only, the process is now described with reference to the drawing. It shows a flow diagram of the improved process according to the invention. The HMTBN represented by (A) is added to the acidification vessel (1), where it is mixed with concentrated sulphuric acid represented by (B). The arrangement of the acidification loop formed by the vessel (1), the pipeworks (C) and (D) and the heat exchanger (E) permits a concentration of sulphuric acid of 20–50% by weight to be obtained within the vessel (1). The reaction mixture passes through the pipework (F) to the hydrolysis reactor (2) in which the reaction is carried out under conditions of temperature and time which were previously specified. The hydrolysis reactor is provided with a line to the atmosphere (G) for ventilation, and outlet pipework (H) which leads to a neutralization and mixing vessel (3) into which the ammonium hydroxide solution is added through (I). If necessary, gaseous ammonia can be added to form the ammonium hydroxide solution in situ. From vessel (3), the neutralized solution passes by the pipework J) to the phase decanting vessel (4), in which the organic phase (Ph O) and the aqueous phase (Ph A) form.

The organic phase (Ph O) is passed through the pipework (K) to vacuum vaporizer (7), provided with its steam inlet (EV) for heating, with its outlet for the vacuum (SV) and with its pipework (N) for aqueous effluent. A conveyable suspension is discharged through the pipework (M), being formed from ammonium sulphate and HMTBA. This suspension enters the separating device (filter/centrifuge) (8), enabling on the one hand a solid cake of impure ammonium sulphate containing HMTBA to be recovered. The cake is conveyed by the means represented by (O) to the dilution vessel (10), from which a solution of ammonium sulphate containing a small proportion of HMTBA is discharged through the pipework (P). This solution is recycled to the neutralization vessel (3). On the other and, liquid HMTBA is drawn through the pipework (Q) from the separating device (8). This liquid, after being diluted with water in the mixer (9) to adjust its concentration and possibly being stabilized with sulphuric acid, is collected as the principal product of the process.

The aqueous phase (Ph A), which is drawn from the decanting vessel (4) through the pipework (L), is concentrated in the vaporizer (5). Here, the labels SV and EV have the same meanings as with the vaporizer (7). The aqueous effluent is collected through the pipework (R). An aqueous suspension of impure ammonium sulphate containing HMTBA is collected through (S). The suspension is separated by filtration and/or centrifugation in (6) to remove ammonium sulphate byproduct which, after drying, can be used as a fertilizer. The aqueous liquid which contains ammonium sulphate, which has not been precipitated and dissolved HMTBA, is returned through the pipework (T) to the neutralization vessel (3).

In the diagram in the drawings, only the principal elements have been shown. The usual devices and accessories have been deliberately omitted, for example pumps, throughput meters, heating facilities, temperature-measuring devices, etc.

As can be seen, the improved process according to the invention does not in practice permit HMTBA to be lost in effluent flows. It is possible to obtain a yield of 99%.

The improved process according to the invention is extremely advantageous in comparison with the prior art. Indeed, the U.S. Pat. No. 2,745,745 describes a process for obtaining a salt of an alkaline earth metal, the calcium salt of the acid HMTBA, by hydrolysis of HMTBN in two steps, passing through the corresponding amide, and obtaining the salt by adding a hydroxide or a carbonate of the alkaline-earth metal. This method has the disadvantage of requiring alteration of hydrolysis conditions of HMTBA, initially to obtain the corresponding hydroxy-amide and subsequently, under other conditions, to obtain HMTBA. Applicants have found that the solution acidified by their process can be hydrolysis in a single step with practically quantitative yields. This is also valid for the U.S. Pat. No. 2,938,053 which relates essentially to the synthesis of HMTBA, passing through the hydroxy-amide intermediate, to obtain the calcium salt of HMTBA. U.S. Pat. No. 2,745,745 uses a solution of calcium hydroxide or calcium carbonate, to neutralize the sulphuric acid used in the hydrolysis. This method has the advantage of requiring separation of the corresponding calcium sulphate from the remainder of the solution. Moreover, this sulphate precipitates in very fine form, which entrains considerable losses of product in the cake obtained. Further, the corresponding alkaline salt of HMTBA is obtained in impure form, requiring the filtrate to be heated while adding more hydroxide or carbonate, which complicates the process and makes it more expensive. U.S. Pat. No. 2,745,745 also discloses that the free acid can be obtained directly from the hydrolyzed material by extraction with a solvent which is immiscible with water. However, it seems that the yields obtained by the extractive process described in this patent are low. It is thus doubtful whether the process has a practical use.

The U.S. Pat. No. 3,175,000 improves the yield in obtaining the calcium salt of HMTBA by the following means: addition of ammonium sulphate to the hydrolysis material until saturation; extraction of the aqueous phase with a polar solvent which is immiscible with water, preferably an ether; mixing the extract with the organic phase; evaporation of the solvent; and addition of a calcium hydroxide or carbonate to form the salt of HMTBA.

British Patent No. 722,024 also provides calcium sulphate in the final product having the previously mentioned problems.

European Patent Application Nos. 142,448 and 143,100 describe liquid-liquid extraction processes using a solvent which is immiscible with water to separate the salts formed during the hydrolysis of HMTB. They disparage the evaporation process because of the development of a more intense color and a greater content of oligomers, resulting from a high consumption of energy and problems during separation of the salts. Applicants' process obviates all these critical points in these applications, because there is no increase in color or oligomers if the evaporation is carefully carried out at the temperatures recommended for the process. The consumption of energy is less because a solvent-water azeotrope does not have to be evaporated. It is apparent that in applicants' process of decantation prior to evaporation, only the water contained in the organic phase needs to be evaporated. The process described in the present invention does not use any kind of extraction process using a solvent to improve the yield and/or the quality of the final product, as occurs in the references previously mentioned. In fact, due to an evaporative process which is simple and inexpensive, a product results having characteristics which are as good or even better in color, odor and content of oligomers. Further, the cost and complexity of the plant are lower. The danger from inflammable solvents during their transport, storage and handling is totally eliminated, because applicants' process uses aqueous solutions at all times.

The U.S. Pat. No. 3,773,927 uses hydrochloric acid to hydrolyze HMTBN while improving the process described in U.S. Pat. No. 2,745,745 which use solutions of sulphuric acid as the hydrolyzing agent. In hydrolysis with hydrochloric acid, a solution of HMTBA is obtained having a single phase. All the ammonium chloride produced by the hydrolysis is located in this phase. Thus, the subsequent separating processes are very difficult to carry out with high yields, considering the problems which exist in handling highly viscous suspension. Thus, industrial use seems to have little viability. Further, applicants have been able to verify that hydrochloric acid does not appear to be suitable for carrying out the hydrolysis of the hydroxy-nitrile, considering the large quantity of oligomers formed and considering the strong coloration of the product. This necessitates that it is diluted and heated to 90° C. in the presence of hydrochloric acid, to hydrolyze the oligomers which are formed.

U.S. Pat. No. 4,353,924 enables an aqueous solution of HMTBA to be obtained. However, the principal property sought in the solution is that it should be free of corrosive properties with respect to steel surfaces. Although it is intended to partially neutralize the hydrolysis mixture, this neutralization is not carried out compulsorily after hydrolysis. It can be carried out after dehydration of the solution and before centrifugation, to separate the precipitate salt of the inorganic acid (ammonium chloride, ammonium sulphate, etc...) or else after centrifugation as a final step. From the brief text of this patent, it seems that a low yield in the recovery of HMTBA may be deduced. On the other hand, the neutralization conditions do not permit decantation of the two phases. The problem which this patent claims to resolve appears to be irrelevant as it is necessary to stabilize the aqueous solutions of HMTBA with small quantities of free inorganic acid, to prevent the formation of oligomers.

Thus, the process according to the invention is advantageous in comparison with known processes, as much from the viewpoint of the quality of the product obtained as from the economy of the process. Indeed, the recovery of ammonium sulphate byproduct is carried out exclusively from the decanted aqueous phase in which the concentration of HMTBA is low, so that the recovery of HMTBA s the principal product and of ammonium sulphate as byproduct is practically quantitative.

EXAMPLES

The invention is now described by the following examples, none of which has a limiting character.

EXAMPLE 1

200 g of 3-methylthio-propionaldehyde, together with 0.4 ml of pyridine are added to a reactor provided with a thermostatically controlled mantle, a stirrer, a thermometer and a feed hopper. While maintaining the temperature at 20° C. by recycling glycol/water mixture through the mantle of the reactor, 300 g of aqueous solution of 20% hydrocyanic acid are added. Care is taken during the addition of this acid that the temperature should not be exceeded. Subsequently the temperature is increased to 45° C. and kept there for 15 minutes.

In the same reactor an under vigorous agitation, 175 g of 98% sulphuric acid is added at the maximum rate of addition which is compatible with not exceeding the temperature of 50° C. After the addition of acid, the temperature is kept at 50° C. for a further 30 minutes. Then the temperature is quickly raised to 90° C. and kept there for 120 minutes while at the same time applying a slight vacuum to the reactor. During this time 60 g of condensate are removed. At the conclusion of the hydrolysis reaction, the sulphuric acid present in the reaction material is neutralized with ammonium hydroxide of 25% concentration and the separation of the two phases formed by decantation is begun. The temperature for neutralization and decantation did not exceed 70° C.

The aqueous phase which had been decanted is led into a turbo-evaporator in which, due to the application of vacuum, 266 g of water are evaporated and 231 g of ammonium sulphate are precipitated, being recovered by filtration. 52 g of mother liquors taken from filtration of the ammonium sulphate are kept for recycling in the subsequent Example 2 (recycling material 1).

The water present in the organic phase is eliminated by evaporation under vacuum, and the suspension of ammonium sulphate is filtered, providing in this way 117 g of cake and 287 g of HMTBA. The cake is dissolved in 233 g of water and kept for recycling in the subsequent Example 2 (recycling material 2). By analysis of the HMTBA obtained, it is found that it contained 80% by weight of HMTBA monomer, 12% by weight of oligomers, 1.1% of water and 0.8 of sulphate ions. The HMTBA obtained is diluted and stabilized with water which had been acidified with sulphuric acid, to obtain a product containing 88% of HMTBA, 0.7% of ammonium sulphate, 0.3% of free sulphuric acid and having a coloration, which is less than 2,000, measured in degrees APHA.

EXAMPLE 2

125 g of technical grade (98%) 3-methylthiopropionaldehyde and 0.3 ml of pyridine are added to a reactor provided with a thermostatically controlled mantle, a stirrer, a thermometer and a feed hopper. While cooling the reactor using glycol/water mixture at $-10°$ C., 188 g of an aqueous solution of 20% hydrocyanic acid are added over a time no less than 20 minutes. After this period, the temperature of the reaction material is increased to 45° C. in 10 minutes and the material is kept at the temperature for a further 30 minutes.

Subsequently, 131 g of sulphuric acid of 98% concentration are added while keeping the mixture under violent agitation and cooled to 50° C. in a continuous addition loop, in which the mixture is kept under agitation for a further 30 minutes. The acidified material is subsequently heated to 90° C. and kept at the temperature for 180 minutes while eliminating, due to placing the reactor under vacuum, 32 g of water and volatile matter during the first 60 minutes. For the remainder of the time the reactor is kept boiling under reflux at the given temperature and under a slight vacuum. On conclusion of the hydrolysis reaction, recycling materials 1 and 2 are added. Then the sulphuric acid is neutralized by adding an aqueous solution of 25% ammonia while cooling so as not to exceed the temperature of 70° C. The two phases are decanted wile maintaining the temperature. By decantation, 414 g of aqueous phase is obtained including 192 g of ammonium sulphate corresponding to 72% of the total, and 381 g of organic phase containing the remainder of the ammonium sulphate and 198 g of HMTBA, corresponding to 94% of the total.

Ammonium sulphate is precipitated from the aqueous phase, by evaporation under vacuum of 90% of the water present. After drying, 172 g of ammonium sulphate are obtained having a purity greater than 99.5%. The recovery yield is greater than 99%. The 52 g of mother liquors taken from filtration of the suspension are recycled in the subsequent reaction to the level of the mixing reactor and form the recycled material in pipe Water is eliminated from the organic phase by distillation to dryness under vacuum, and 179 g of HMTBA are obtained having a purity of 98.5% and 102 g of cake containing 73% of ammonium sulphate and 27% of HMTBA. The cake is dissolved in a small quantity of water and recycled in the subsequent reaction, to the level of the mixing reactor, for recovery. This solution corresponds to the recycled material in pipe (P) in the diagram in the drawings. The HMTBA is adjusted with water which had been acidified with sulphuric acid to give 200 g of a stable aqueous solution having a concentration of 88% by weight of HMTBA, a coloration of 1,800 degrees APHA and a viscosity of 75 centistokes. By specific quantitative analysis for the HMTBA monomer in the final product, it is confirmed that it did not contain less than 80% of this monomer.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. An improved process for preparation of aqueous solutions of 2-hydroxy-4-methylthio-butyric acid (henceforth designated HMTBA) resulting from the hydrolysis reaction, in a single step, of 2-hydroxy-4-methylthio-butyronitrile with sulphuric acid, comprising the following operations being carried out:
   (a) neutralization of an acid mixture resulting from the hydrolysis reaction and recycled materials with ammonium hydroxide, so as to form two phases, an organic phase containing a major proportion of HMTBA and a minor proportion of ammonium sulphate, and an aqueous phase containing a major proportion of ammonium sulphate and a minor proportion of HMTBA;
   (b) separation of the two phases;
   (c) precipitation of ammonium sulphate from the aqueous phase by evaporation of water, at atmospheric pressure or reduced pressure, followed by separation of the ammonium sulphate by filtration and/or centrifugation, and recycling to a neutralization reactor for the resulting liquid which contains unprecipitated ammonium sulphate and dissolved HMTBA;
   (d) concentration of the organic phase by evaporation of the water contained in this phase to obtain a suspension of HMTBA containing a residual portion of ammonium sulphate;
   (e) separation by centrifugation and/or decantation of the suspension resulting from the previous operation to obtain an HMTBA which is practically devoid of ammonium sulphate and a cake of impure ammonium sulphate containing HMTBA;
   (f) dissolving the cake of impure ammonium sulphate obtained in the previous operation in water, and recycling the resulting solution to the neutralization reactor; and
   (g) diluting the HMTBA obtained in step (e) with water.

2. The process according to claim 1, further comprising stabilizing the diluted HMTBA with sulphuric acid.

3. The process according to claim 1, further comprising using the ammonium hydroxide in the neutralization operation (a) having a concentration of 20-35% by weight.

4. The process according to claim 3, wherein the ammonium hydroxide is obtained by injection of gaseous $NH_3$ into the hydrolysis reaction mixture.

5. The process according to claim 1, further comprising controlling the temperature of the mixture during neutralization so that it does not exceed approximately 70° C.

6. The process according to claim 1, wherein in operation (d), the proportion of water in the organic phase is brought to a value of 0.5-1% by weight by evaporation under reduced pressure.

7. The process according to claim 1, further comprising recovering the ammonium sulphate produced in operation (c), after separation and drying, as a by-product practically devoid of HMTBA.

* * * * *

UNITED STATES PATENT AND TRADEMARK OFFICE
CERTIFICATE OF CORRECTION

PATENT NO. : 4,912,257

DATED : March 27, 1990

INVENTOR(S) : Hernandez, et al.

It is certified that error appears in the above-identified patent and that said Letters Patent is hereby corrected as shown below:

Column 1, line 27, change "a" to --as--.
Column 1, line 54, change "organic" to --inorganic--.
Column 1, line 65, change "hydoolysis" to --hydrolysis--.
Column 2, line 52, change "(HMTBA)" to --(HMTBN)--.
Column 2, line 54, change "393,825" to --393,824--.
Column 3, line 60, change "aid" to --acid--.
Column 4, line 30, change "separate" to --separated--.
Column 4, line 45, change "an" to --and--.
Column 5, line 24, change "and" to --hand--.
Column 7, line 36, change "s" to --as--.
Column 7, line 56, change "an" to --and--.
Column 8, line 68, after "pipe" insert --(T) in the diagram in the drawings.--

Signed and Sealed this

Thirteenth Day of August, 1991

*Attest:*

HARRY F. MANBECK, JR.

*Attesting Officer*  *Commissioner of Patents and Trademarks*